United States Patent [19]

Fillit et al.

[11] Patent Number: 4,985,542

[45] Date of Patent: * Jan. 15, 1991

[54] KIT FOR THE DETERMINATION AND DIAGNOSIS OF NON-GOODPASTURE GLOMERULONEPHRITIS

[75] Inventors: Howard Fillit; Shridhar P. Damle; John Zabriskie; John D. Gregory, all of New York, N.Y.

[73] Assignee: The Rockefeller University, New York, N.Y.

[*] Notice: The portion of the term of this patent subsequent to Jul. 18, 2006 has been disclaimed.

[21] Appl. No.: 352,727

[22] Filed: May 17, 1989

Related U.S. Application Data

[62] Division of Ser. No. 618,500, Jun. 8, 1984, Pat. No. 4,849,339.

[51] Int. Cl.$^5$ .................... C07K 15/14; C07K 3/00; A61K 39/00; A61K 35/12
[52] U.S. Cl. .................... 530/395; 424/88; 424/558; 435/810; 436/808; 530/412; 530/417; 530/422; 530/806; 530/835
[58] Field of Search ............... 530/395, 412, 417, 422, 530/806, 835; 424/88, 103; 435/810; 436/808

[56] References Cited

PUBLICATIONS

Kefalides, Connective Tissue Res., 1:3–13, "The Chemistry of Antigenic Components Isolated From Glomerular Basement Membrane", (1972).

Kanwar et al., Chemical Abstracts 95: 110476d, 245, "Partial Characterization of Newly Synthesized Proleoglycans Isolated From the Glomerular Basement Membrane", (1981).

Kanwar, Y., et al. (1981) The Journal of Cell Biology, vol. 90, pp. 527–532.

Primary Examiner—Esther L. Kepplinger
Assistant Examiner—Florina B. Hoffer
Attorney, Agent, or Firm—Felfe & Lynch

[57] ABSTRACT

Purified glomerular proteoglycans are used as a basis for a diagnostic test for glomerulonephritis in humans involving an immunological reaction between the purified proteoglycans and patient area. A new method for purification of glomeruli proteoglycan antigens is described using guanidine extraction.

1 Claim, No Drawings

KIT FOR THE DETERMINATION AND DIAGNOSIS OF NON-GOODPASTURE GLOMERULONEPHRITIS

This invention was made with government support under PHSSK08AM00981 from the National Institutes of Health. Therefore, the government has certain rights in this invention.

This is a divisional of application Ser. No. 618,500, filed June 8, 1984, and now issued as U.S. Pat. No. 4,849,339.

This invention relates to a diagnostic method for glomerulonephritis.

SUMMARY

Purified glomerular proteoglycan antigens serve as the basis for an immunological test in patients with various forms of acute and chronic renal disease.

DESCRIPTION

Studies of humoral autoimmunity in glomerulonephritis (GN) have revealed the importance of antibodies directed against a noncollagenous glomerular basement membrane (GBM) antigen, termed Goodpasture's antigen, in patients with rapidly progressive glomerulonephritis (Wilson, C. B., et al. (1973) *Kid. Int.* 3:74–89.). These antibodies are found in only about 1% of all patients with glomerular disease. One protein presumably representing Goodpasture's antigen has been isolated with an apparent unit molecular weight of 26,000 (Weislander, J., et al. (1984) *Proc. Nat. Acad. Sci.* 81:1544–1548). A diagnostic based on a more prevalent antigen or antigenic determinant in GN would be more useful. Evidence suggesting that humoral autoimmunity may be present in a broader spectrum of patients comes from earlier studies (Liu, C.T., et al. (1958) *J. Immunol.* 81:492–498; Kramer, N.C., et al. (1961) *Am. J. Med.* 30:39–45; Lange, K., et al. (1949) *J. Clin. Invest.* 28:50–55; Chudomel, V., et al. (1961) *Lancet* ii: 965–967) in which autoantibodies to crude kidney antigen were found in patients with acute and chronic GN. Other glomerular antigens may be the focus of glomerular autoimmunity (Weislander, J., et al. (1983) *Kid. Int.* 23:855–861; Foidart, J.B., et al. (1980) *Kid. Int.* 18:136; Wick, G., et al. (1980) *Clin. Exp. Immunol.* 39:733–740).

Antibodies to GBM antigens solubilized by guanidine, pepsin or collagenase digestion were found in patients with systemic lupus GN, IgA nephropathy, and polyarteristis nodosa (Weislander, J. et al. (1983) Supra), and the presence of autoantibodies to laminin and type IV collagen were noted in patients with Goodpasture's syndrome (Foidart, J.B., et al. (1980) Supra), although others have not found anti-laminin or anti-type IV collagen reactivity (Wick, G., et al. (1980) Supra).

Cellular autoimmunity to glomerular antigens has been shown using a variety of cellular assays in a spectrum of histologic types of human GN, including patients without clinical or histologic features of Goodpasture's disease (Fillit, H.M., et al. (1982) *Am. J. Path.* 109:227–243; Bendixen, G., (1968) *Acta. Med. Scand.* 184:99–103; Rocklin, R., et al. (1970) *New Engl. J. Med.* 248:498–501; Dardenne, M., et al. (1970) *Lancet* i:1-26–128; Mahieu, P., et al. (1972) *Am. J. Med.* 53:185–192; Macanovic, M., et al. (1972) *Lancet* ii:2-07–210; Mallick, N., et al. (1972) *Lancet* i:507–509; Fillit, H.M., et al. (1978) *N. Engl. J. Med.* 298:861–867; Matsumoto, K., et al. (1978) *Nephron* 21:192–200; Matsumoto, K., et al. (1982) *Nephron* 30:205–209). Cellular reactivity to crude GBM antigens has been found in patients with various forms of chronic GN (Fillit, H.M., et al. (1978) Supra) who did not have antibodies against Goodpasture's antigen (Fillit, H. M., et al. (1978) *Kid. Int.* 14:710). Whether cellular autoimmunity occurs to antigens to which no humoral immune response is made, or to antigens which have not been identified for humoral testing, remains unknown. Autoimmunity to a variety of glomerular antigens may occur in a spectrum of histologic types of acute and chronic GN.

We have isolated soluble anionic glomerular antigens and demonstrated humoral autoimmunity to these antigens in patients with various forms of acute and chronic renal disease in the present invention. Biochemical characterization of these anionic antigens indicates that they are proteoglycans. The glycosaminoglycan chains, specifically heparan sulfate, appear to be the primary site of immune reactivity. Purified human umbilical cord hyaluronate and purified streptococcal hyaluronate also inhibit the observed reactivity to the proteoglycan material, albeit to a lesser degree, indicating cross-reactivity in the immune response to glomerular heparan sulfate, tissue hyaluronate, and streptococcal hyaluronate in patients with acute poststreptococcal glomerulonephritis (APSGN). A second immunoreactive site of the glomerular proteoglycan appears to be related to N-acetylgalactosamine. Glomerular autoimmunity may also be directed to the protein portion of the proteoglycan.

Subjects: Patients with chronic renal disease were seen in The Rockefeller University Clinic or at The New York Hospital. Only patients with chronic renal disease who had renal biopsies as part of their medical evaluation were entered into our study. Patients with acute poststreptococcal GN (APSGN) and chronic poststreptococcal GN (CPSGN) were seen in San Fernando, Trinidad, as part of a collaborative effort with Dr. Theo Poon-King. All of these patients had extensive clinical studies, including antistreptolysin 0 titers and streptococcal cultures, to document the presence of APSGN. Dr. Luis Tapia provided sera from patients on hemodialysis.

DEAE-Sepharose CL-6B and Sepharose CL-4B were obtained from Pharmacia. Chondroitinase ABC was purchased from Miles Laboratories. DEAE-Cellulose, pepstatin A, benzamidine-HCl, 6-aminohexanoic acid, guanidine-HCl (Grade 1), phenylmethylsulfonyl flouride, N-ethylmaleimide, diatomaceous earth (grade I), were purchased from Sigma. Papain (twice crystallized) was a product of Worthingon Biochemicals. Urea (Fisher, certified ACS) as an 8M solution was passed through a Fisher high capacity deionizing cartridge shortly before use. Purified glycosaminoglycans (GAG's) were obtained from Allen Horowitz, University of Chicago, Chicago, Illinois. These included chondroitin-4-sulfate and chondroitin-6-sulfate (S. platorhyncus), hyaluronate (human umbilical cord), dermatan sulfate (hog mucosa), heparin (beef lung), and heparan sulfate (beef lung). Group A streptococcal hyaluronate and group A, A variant, and C carbohydrates were obtained from Dr. Maclyn McCarty. N-acetylglucosamine, N-acetylmannosamine, N-acetylgalactosamine and D-glucuronic acid were obtained from Sigma.

Isolation of glomerular proteoglycans from whole glomeruli by guanidine-HCl extraction: Glomeruli were isolated from fresh bovine and human kidneys by a sieving method (Misra, R.P., (1972) *Am. J. Clin. Path.* 58:135–140). The frozen glomeruli were thawed, and centrifuged at 2,500 rpm for ten minutes. The pellet volume was measured and the pellet diluted 1:100 (v/v) in distilled water containing protease inhibitors (0.1M 6-aminohexanoic acid, 0.005M benzamidine, 0.01M EDTA), stirred magnetically for three hours at 4C, and centrifuged at 12,100 g for ten minutes (Table 1). The pellet was resuspended in 4M guanidine HCl in 0.05M sodium acetate buffer, pH 5.8, with protease inhibitors as described above, stirred magnetically for 48 hours at 4C, and centrifuged as above. A second extraction in the same solvent was performed for 18 hours. The combined supernatants were dialyzed (in Spectrophor 3 membrane tubing) against three changes of ten volumes of deionized 7M urea with 0.01M EDTA, 0.05M Tris HCl buffer, pH 6.5.

A DEAE-Sepharose CL-6B column was prepared, with a bed volume of 80 ml, and washed with four bed volumes of the above urea buffer at 4C. The extract was filtered through diatomaceous earth to remove insoluble material, and the cake was washed thoroughly with the 7M ure buffer. The filtrate was loaded on to the column and eluted stepwise with three column volumes of increasing concentrations of NaCl in 7M urea buffer (from 0.0M to 1.0M NaCl with 0.1M NaCl increments). Each eluate was extensively dialyzed against distilled water and lyophilized. The material eluted with 0.4M, 0.5M, and 0.6M NaCl was redissolved in 0.5M sodium acetate, pH 5.8, and was finally rechromatographed on Sepharose CL-4B (0.78×110 cm) in 0.5M sodium acetate buffer, pH 5.8. Each elution was extensively dialyzed against distilled water and lyophilized.

Preparation of bovine anionic glomerular basement membrane (GBM) antigens: Glomeruli were prepared from fresh bovine kidneys by graded sieving (Misra, R.P., (1972) Supra). The isolated glomeruli were frozen at −70C in 0.15M NaCl with 0.02% azide until further use. For the isolation of GBM, a modification of a previous method (Meezan, E., et al. (1975) *Life Sci.* 17:1721–1732) was used. The glomeruli were thawed and spun at 2000 g for ten minutes in an IEC centrifuge. Pelleted glomeruli were added to distilled water containing 0.02% azide (100:1), stirred magnetically for 2 hours at 4° C, and then centrifuged at 12,100 g for twenty minutes at 4° C. The supernatent was removed, placed in a Spectrophor dialysis membrane (molecular weight cutoff of 3500), dialyzed against distilled water, and lyophilized. Sodium deoxycholate (4% in 0.02% azide) was added to the pellet (40:1, v/v) and stirred for eighteen hours at 4° C. After centrifugation at 12,100 g for twenty minutes, the supernatent was removed and 0.15 M phosphate buffered saline (PBS) containing 3mM $MgCl_2$ was added to the pellet (40:1) v/v) gradually with stirring. DNAase (Sigma, D4638) (1 mg /100 ml PBS) was added, the suspension was stirred magnetically at 4° C. for four hours, centrifuged at 23,000 g for twenty minutes, and the supernatent removed. For extraction of soluble GBM antigens, a modification of a previous method was employed (Kefalides, N.A., (1972) *Conn. Tiss. Res.* 1:3–13). Urea (8M, Aristar) in 0.15 M KP04 pH 5.5 was added to the GBM pellet (50:1, v/v). The GBM-urea mixture was suspended using a waterbath sonicator at room temperature for 15 seconds, and the material gently stirred at 37° C. for eighteen hours. The urea extract was centrifuged at 12,100 g for twenty minutes, and the supernatant was stored at 4° C. Two further urea extractions were performed, and all supernatants were dialyzed against five change of eighteen liters of distilled water (in a Spectrophor 3 dialysis bag with a molecular weight cutoff of 3,500) and subsequently lyophilized. The three extracts were combined, and 300 mg was used for DEAE-Cellulose chromatography.

DEAE-Cellulose (Sigma 8382) was equilibrated in 0.005M sodium acetate pH 5.5 containing 8M urea and was poured into a column 2.7 cm×15 cm, and washed with 100 ml of urea-acetate buffer. The urea extracted material (300 mg) was added to 30 ml of urea-acetate buffer, briefly sonicated in a probe sonicator (Ultrasonics, Plainview, N.Y.) for five seconds to obtain a suspension, and then stirred overnight at 37° C. The suspension was centrifuged at 12,100 g for ten minutes, and the supernatant was loaded on to the DEAE column. A stepwise elution employing three column volumes each of urea-acetate buffer, 0.1M NaCl, 0.3M NaCl, 0.6M NaCl and 1M NaCl in urea-acetate buffer was performed. Fractions (10 ml) were collected, and monitored with a Beckman spectrophotometer at 280 nm. Each step was dialyzed extensively against distilled water (in a Spectrophor 3 membrane tubing), and lyophilized. The material used as antigen was the 0.6M NaCl elution (abbreviated: 0.6M-DE-urea-GBM).

SDS Polyacrylamide gel electrophoresis: The various samples were electrophoresed on SDS polyacrylamide slab gel electrohporesis (SDS-PAGE) using a modification of standard methods (Laemmli, U.K., (1970) *Nature* 227:680–685). Briefly, varying amounts of lyophilized sample were placed in SDS sample buffer without beta-mercaptoethanol. The samples were warmed to 37° C. and dissolved in a waterbath sonicator for ten seconds. A 4–15% gradient gel (0.1 cm. in thickness, 10 cm. in height) with a 3% stacking gel was employed. Electrophoresis was carried out for approximately one hour with 60 ma current. Gels were stained with 0.1% Coomassie brilliant blue R250 in 25% isopropanol-10% acetic acid in distilled water and stained in isopropanol-acetic acid in distilled water. Some gels were stained with Alcian blue by fixing the gels in 0.1N HCl or or 10% acetic acid, followed by the addition of 0.1% Alcian blue in 10% acetic acid containing 0.05M $MgCl_2$ for approximately two hours. Finally, the gels were destained in 0.6N HCl.

Isoelectric focusing: Isoelectric focusing was performed according to described methods (*Isoelectric focusing,* Pharmacia Fine Chemicals, Ljungforetagen AB, Orebro, Sweden, 1982) with an LKB multiphor apparatus. Agarose (1%) in sorbitol was prepared at 100° C. and poured onto Gelbond (LKB). The buffers for the electrodes were 0.1M H and 0.2M histidine. Ampholines 2.5–4.0 and 4.0–6.0 (LKB) were employed at 2%. Focusing was performed at 600 volts for three hours at 5 watts. The gels were fixed in fixing solution (containing 17.3 grams of sulfosalisylic acid, 57.5 gms trichloroacetic acid, and 150 ml methanol, brought to 500 cc total volume with distilled water), and washed twice in ethanol for ten minutes. Finally, the gel was dried by pressing with filter paper using one kilogram for thirty minutes, dried with mild heat, and stained with 0.1% Alcian blue and 0.05% Coomassie Blue R 250 in fixing buffer, and destained in the same buffer.

Immunoblotting: Immunoblotting was performed according to the method of Blake et al ((1984) *Anal. Biochem.* 136:175–179). Briefly, SDS-PAGE was performed as described above. After electrophoresis, the gels were briefly washed in methanol blotting buffer, placed on nitrocellulose paper (Schleicher and Scheull) in a sandwich of Whatman chromatography paper between two sponges, and placed in a blotting apparatus. Blotting was performed with 1.0 amp of current at constant (1 volt) voltage for one hour. The gels were removed, and the nitrocellulose was cut in 1 cm. strips and placed in 0.1M phosphate buffered saline, pH 7.4, containing 0.5% Tween 20 (PBST). The paper was washed in PBST for two washes of 30 minutes each to block nonspecific binding sites. Serum samples were added at varying dilutions in PBST overnight. The paper was then washed three times for five minutes each in PBST and an alkaline phosphatase conjugated goat anti-human IgG (Sigma) was added at a 1:500 dilution in PBST for four hours. The paper was then washed in PBST for three washes of five minutes each, and then washed in PBST for three washes of five minutes each, and then washed in 0.1M veronal acetate buffer, pH 9.6, for five minutes. Finally, a developing reagent containing 40 microliters of 2M MgCl$_2$ 1 ml of 0.1% nitro blue tetrazolium in veronal acetate pH 9.6, and 100 microliters of a 5mg/ml solution of 5-bromo, 4-chloro indoxyl phosphate (U.S. Biochemicals) in dimethylformamide in 9 ml of veronal acetate pH 9.6 was added, and the paper developed for up to one hour.

Enzyme linked immunoassay (ELISA): ELISA was performed essentially according to the methods of Engvall (Engvall, E., et al. (1972) *J. Immunol.* 109:129-142) with Nunc immunoplates. Various amounts of antigen were placed in wells of the plates in 50 microliters 0.1M Tris HCl buffer, pH 9.6, containing 0.3 MgCl$_2$ overnight at 4° C. The plates were then washed once with PBS containing 0.5% Brij (PBSB). Brij 35 is a trademark of Pierce Chemical Co., Rockford Illinois and is a 30% solution of polyoxyethylenelauryl ether detergent. Finally, the nonspecific sites on the plates were blocked by two further incubations with PBSB for thirty minutes each. Serum was diluted in PBSB and 50 microliters added to the plates for four hours. The plates were washed by adding 250 microliters 0.9% NaCl containing 0.5% Brij for three washes of five minutes each. An alkaline phosphatase conjugated goat anti-human IgG (gamma chain specific) antiserum (Sigma, lot 88F 9350) was added at a dilution of 1:1000 in 50 microliters PBSB for four hours. The plates were washed in saline-Brij as above three times for five minutes each. Finally, a developing substrate was added. 10 mg of nitrophenyl phosphate (Sigma) per ten ml of diethanolamine buffer (containing 97 ml diethanolamine, 1 ml of 1M MgCl$_2$, 1 ml of 0.1M zinc acetate, 0.2 gm sodium azide, and 800 ml of distilled water, pH 9.8) was prepared. 150 microliter of nitrophenyl phosphate diethanolamine developing reagent was added, and the plates were read at 405 nm in a Titertek ELISA plate reader at intervals for up to four hours. Results are expressed as the titer which is the reciprocal of the dilution giving an absolute spectrophotometric reading of 1.0 at 405 nm.

Preparation of rabbit antisera to GBM: New Zealand white female adult rabbits were immunized with whole bovine and human GBM extracted by a standard Meezan (Meezan, E., et al. (1975) *Life Sci.* 17:1721-1732) extraction using deoxycholate as originally described. One mg of GBM in complete Freund's adjuvant was injected intradermally into two rabbits at three week intervals for a total of three injections. Serum was harvested one week after the final injection.

Chemical composition of antigenic preparations: Uronic acid was measured by a variation of the borate/carbazole method (Bitter, T., et al. (1962) *Anal. Biochem.* 4:330-334). Hexosamines were quantitated on a Technicon TSM amino acid analyzer after hydrolysis in 4M HCl at 100 C for 8 hours (Kieras, F. J., (1974) *J. Biol. Chem.* 249:7506-7513). Protein was measured by a modified Lowry procedure (Schacterle, G.R., et al. (1973) *Anal. Biochem.* 51:654-655) or by absorbance at 280 nm. Digestion of proteoglycans with chondroitinase ABC (0.1 unit/mg) was done in 0.1M sodium acetate, 0.1M Tris-HCl, containing the following protease inhibitors: 10 mM EDTA, 10 mM N-ethylmaleimide, lmM phenylmethylsulfonyl fluoride, and 0.035 mM pepstatin A, pH 7.3 at 37° C. for four hours. Digestion of proteoglycans with papain was carried out in 0.1 M potassium phosphate, 0.01M EDTA, 0.01M cysteine, pH 6.8, at 64° C. for 18 hours. The ratio of proteoglycan to papain was 100:1. Nitrous acid treatment of proteoglycans was carried out according to the procedure described by Shively and Conrad (Shively, J., et al. (1976) *Biochemistry* 5:3932-3942). The digests were chromatographed on Sepharose CL-4B in 0.5M sodium acetate pH 5.8. Intact preparations used as controls were chromatographed under identical conditions.

The examples below serve to illustrate the invention without limiting the scope of the invention.

The information in this specification is incorporated in a paper submitted to the Journal of Clinical Investigation by Howard Fillit et al. entitled "Antibodies to Glomerular Proteoglycans", which paper is hereby incorporated by reference.

EXAMPLE I

Isolation of glomerular proteoglycans by guanidine-HCl extraction: A direct 4M guanidine extraction of whole glomeruli after hypotonic lysis was performed. The guanidine extract was fractionated by DEAE-Sepharose CL-6B chromatogrpahy, and 0.4M, 0.5M and 0.6M NaCl eluates were further chromatographed on Sepharose CL-4B. This scheme is summarized in FIG. 1 for the bovine material (note abbreviations used in the table for these antigens. The first number indicates the molar NaCl elution of DEAE-Sepharose CL-6B chromatography; the second number indicates the peak of Sepharose CL-4B chromatography. For example, 0.4M-peak II represents the 0.4M NaCl eluate of DEAE-Sepharose CL-6B chromatography which has been further chromatographed on Sepharose CL-4B and isolated as peak II). A similar extraction was employed with human glomeruli. However, enough human material was not available for Sepharose CL-4B chromatography. Thus, the 0.6M NaCl eluate of DEAE-Sepharose CL-6B chromatography (abbreviated: human-DE-0.6M) was used as antigen for these studies.

The distribution of hexosamine-containing compounds as measured by aminosugar analysis (Kieras, F. J., (1974) *J. Biol. Chem.* 249:7506-7513) of the extract after DEAE Sepharose CL-6B ion -exchange chromatography is shown in Table I. Percentage of glucosamine and galactosamine in regard to total amino sugar are determined in Table I. The glucosamine content of the unabsorbed and 0.1M NaCl eluates probably represents non-charged glycoproteins and possibly non-sulfated glycosaminoglycans (free or protein bound). The major hexosamine-containing material emerged in 0.4M, 0.5M and 0.6M NaCl eluates. A small amount of glucosamine was present in higher salt concentrations.

The 0.4M, 0.5M and 0.6M NaCl eluates from the above CL-6B were purified further by chromatography on Sepharose CL-4B. All eluates were found to have identical profiles. A typical profile (0.4M NaCl eluate) shows resolution of the material into three protein peaks. Peak I emerges in the void volume (v·) of the column and contains only glucosamine. Peak II, (Kav=0.48) emerges in fractions 45–63 with a peak about fraction 54, contains both glucosamine and galactosamine in an approximate ratio of 4.5 to 1 respectively. Uronic acid was also present in peak I and peak II. Peak III eluting at approximately fraction 85 (Vt) has a large amount of protein or peptides but no hexosamines. Peak III material was not studied further $$\left( Kav = \frac{V\text{peak} - Vo}{Vt - Vo} \right).$$

EXAMPLE II

The material in peak I and II above were identified as proteoglycans by their susceptibility to specific enzymatic and chemical treatments. If the treated material in each case was susceptible, it moved to a chromatographic position on Sepharose CL-4B with a much higher Kav than before treatment. All fractions were degraded by papain indicating their protein content. As seen in Table II, only a glucosamine-containing component was present in Peak I, and it was susceptible to nitrous acid indicating the presence of a heparan sulfate proteoglycan. In peak II, a glucosamine-containing proteoglycan susceptible to nitrous acid, and a galactosamine-containing proteoglycan susceptible to chondroitinase ABC were present, indicating a mixture of heparan sulfate and chondroitin or dermatan sulfate proteoglycans, or possibly a hybrid molecule with both kinds of GAG. The distribution of proteoglycans in three salt concentrations from the ion exchange column may reflect heterogeneity caused by variable degrees of sulfation of GAG's or variable amounts of sialic acid substitution on the oligosaccharide chains that are present in most proteoglycans. Further characterization of the glomerular proteoglycans is in progress.

EXAMPLE III

SDS-PAGE analysis of the purified 0.4M-peakII material revealed only high molecular weight material (greater than 200,00 M.W.) which electrophoresed as a broad band in the gradient gel, and which was stained more intensely by Alcian blue than Coomassie blue. This is consistent with the fact that protein-polysaccharide complexes do not stain well with Coomassie blue, and are stained more intensely with the cationic dye, Alcian blue. Isoelectric focusing followed by staining with both Alcian blue and Coomassie blue in separate gels revealed that the pI of the isolated 0.4M-peak II fraction was between 2.94 and 3.53. Molecular weight markers are phosphorylase B relative M.W. 94,000, serum albumin relative M.W. 67,000. These studies further demonstrated the purity and highly anionic nature of the isolated 0.4M-peakII fraction.

SDS-PAGE analysis of the anionic GBM fractions obtained by DEAE-Cellulose ion exchange chromatography revealed that the 0.3M and 0.6M elutions contained primarily high molecular weight (greater than 200,000) material which failed to form a distinct band, and which stained with both Coomassie and Alcian blue, indicating the presence of anionic protein material. Analysis of the 0.6M elution revealed the presence of a large amount of glucosamine, a small amount of galactosamine, and a high content of uronic acid, indicating that this material was proteoglycan in nature.

EXAMPLE IV

Immunoblot screening studies of the DNase-1M NaCl and sodium deoxycholate extracts removed during the isolation of GBM revealed substantial quantities of high molecular weight broad banded antigenic material in these fractions. An analysis of the hexosamine content of these extracts confirmed the presence of significant amounts of both total hexosamine (both glucosamine and galactosamine) and sulfated GAGs (Table III). Nearly 80% of the total hexosamine and sulfated GAG content of whole glomeruli was demonstrated in the sodium deoxycholate extraction. A further 4M guanidine extract of the isolated GBM contained only 14% of the total hexosamine. Thus, major losses of glomerular hexosamine and sulfated GAGs were apparent in the deoxycholate extraction procedure for the isolation of GBM, with most of the lost material appearing in the deoxycholate fraction.

EXAMPLE V

All of the purified proteoglycans obtained after Sepharose CL-4B chromatography (FIG. 1) were tested by the ELISA. Sera from patients with well documented APSGN, CPSGN and chronic GN (CGN) were studied. Analysis of our results thus far indicates that all of the anionic (0.4–0.6M NaCl) Sepharose CL-4B fractions give similar results using patient sera. Thus, although the various anionic fractions were heterogeneous in their degree of sulfation, and therefore eluted in different (0.4–0.6M) molar NaCl elutions from the DEAE-Sepharose CL-6B column, they appeared antigenically similar. The 0.4M-peak II antigen was most extensively studied and reported in detail here. An immunoblot of the purified 0.4M-peakII antigen stained with the sera from patients with APSGN shows immunostaining of the broad banded high molecular material with the APSGN patient sera, but not with the control serum or the alkaline phosphatase conjugated anti-human IgG antiserum.

EXAMPLE VI

Using ELISA, the 0.4M-peakII antigen was titrated from 10 to 0.1 micrograms per milliliter and tested with the sera from a patient with APSGN and a control. In this experiment, a clear titration effect was seen as the antigen concentration was changed, indicating that ELISA reactivity was directed against the antigen being used to coat the plates (Table IVa). In another representative experiment (Table IVb), a clear titration curve of reactivity is seen as the serum is diluted and the 0.4M-peakII antigen concentration held constant, indicating that IgG in the serum being tested accounted for the observed antibody binding. Titers of the APSGN sera were higher than the CPSGN sera, while controls were seen to contain little or no ELIS reactivity.

Both IgG and IgM antibodies to the 0.4M-PeakII antigen were found in patient sera.

Further testing of the 0.4M-peakII antigen using patient sera showed that 5/7 patients with APSGN, 6/9 patients with CGN, and 0/10 controls were positive (defined as serum titer greater than 1:20) (Table V). For the 0.5M-peakII (Table V) similar findings were noted. In addition, when patients with CPSGN were tested to 0.5M-peakII, 6/11 patients were noted to be positive. Although the amount of material available for testing of the 0.4M-peakI and the 0.5M-peakI were limited, similar ELISA results with patient sera were obtained. In summary, these data indicate the presence of antibodies in the sera of patients with various types of GN reactive with purified bovine anionic glomerular proteoglycan fractions which are antigenically similar, but are heterogeneous with regard to their charge. Since the peak I fractions contained no galactosamine and represented purified heparan sulfate proteoglycan, immunoreactivity to purified heparan sulfate proteoglycan was demonstrated. In addition, immunoreactivity was noted to proteoglycan antigen which contained both glucosamine and galactosamine (peak II).

EXAMPLE VII

Rabbit antisera made to both bovine and human whole GBM demonstrated reactivity to the bovine 0.4M-peakII material in ELISA studies (10 microgram/ml—Table VI). As the rabbit antisera made to human GBM reacted with the bovine antigen, cross-reactivity of the bovine 0.4M-peakII material with the equivalent human antigen is apparent. In addition, human DE-0.6M was also tested in the ELISA. Reactivity of patient sera was observed. A serum from a patient with APSGN reacted to the human antigen in titers approximating that found with bovine (0.4M-peakII) antigen (titer=96). Thus, the bovine and human glomerular proteoglycan preparations demonstrate cross-reactivity on immunologic testing.

EXAMPLE VIII

Various controls were performed to specifically determine whether the ELISA reactivity we noted to the purified proteoglycans was due to nonspecific ionic binding of cationic IgG or due to specific binding of antibody to antigenic sites of these anionic molecules. The inhibition studies were performed in both the immunoblotting and the ELISA using high concentrations of NaCl (up to 1M) to inhibit binding of the 0.4M-peakII material (10 microgram/ml). Essentially no inhibition was seen (Table VII). Preincubation of the 0.4M-peakII material (62.5 micrograms per milliliter) with APSGN sera (1:40) in equal volumes for one hour at room temperature and thirty minutes at 4° C. resulted in specific inhibition of 90% of the serum reactivity to the 0.4M-peakII material further demonstrating the specificity of ELISA activity.

EXAMPLE IX

Inhibition ELISA experiments with purified GAG's revealed inhibition of APSGN serum (1:40) reactivity to human DE-0.6M (10 microgram/ml) primarily with heparan sulfate, and not with other GAG's (Table III). The APSGN serum (1:40) was pre-incubated with various purified glycosaminoglycans at varying concentrations (chondroitin-4-sulfate, chondroitin-6-sulfate, heparin, bovine hyaluronate and heparan sulfate). However, further inhibition studies with the human DE-0.6M (10 microgram/ml) revealed inhibition with both streptococcal and human umbilical cord hyaluronate, although at significantly higher concentrations of inhibitor than with heparan sulfate. Table IX illustrates an APSGN serum (1:40) pre-incubated with heparan sulfate glycosaminoglycan, bovine hyaluronate and streptococcal hyaluronate at varying concentrations. Similar ELISA inhibition findings were noted with the purified bovine 0.4M-peakII proteoglycan. Elisa studies were done with 0.4M-peakII antigen at 10 microgram/ml. An APSGN sera (1:40) was preincubated with various inhibitors including dermatan sulfate, N-acetyglucosamine N-acetylgalactosamine, streptoccal hyaluronate and heparan sulfate at varying concentrations (Table X). Since hyaluronate and heparan sulfate GAG's differ primarily in their degree of sulfation, these findings would suggest that sulfation of the heparan sulfate GAG chains plays an important role in their antigenicity. In addition, cross-reactivity of heparan sulfate and hyaluronate appears to be present.

EXAMPLE X

Further inhibition experiments with N-acetylgalactosamine alone at concentrations of 0.5M showed approximately 50% inhibition of APSGN serum (1:40) reactivity to 0.4M-peakII antigen, while N-acetylglucosamine, D-glucuronic acid, and N-acetylmannosamine showed little inhibition at this concentration. Group C streptococcal carbohydrate (50 mg/ml), whose immunodominant carbohydrate is a terminal N-acetylgalactosamine, also inhibited approximately 50% of APSGN serum (1:40) reactivity (Table XI). Group A (immunodominant site containing terminal N-acetylglucosamine) and A variant (immunodominant site containing primarily rhamnose) streptococcal carbohydrate (50 mg/ml) showed little inhibition. The combined use of streptococcal hyaluronate (5 mg/ml) and N-acetylgalactosamine (1M, 222 mg/ml) resulted in additive inhibition of serum reactivity (Table X). Galactosamine containing GAG's such as chondroitin sulfate have thus far shown little immunoinhibition of serum reactivity, while in one experiment dermatan sulfate showed minor inhibition at higher concentrations (5 mg/ml). Thus, these data indicate the presence of a second antigenic site on the glomerular proteoglycan whose immunodeterminant is N-acetylgalactosamine.

EXAMPLE XI

The possibility that the serum reactivity to proteoglycan might be due to cationic immune complexes was investigated, particularly since we known that the APSGN sera contain high titers of immune complexes (Van de Rijn, et al. (1978) Clin. Exp. Immunol. 34:318-325). Polyethylene glycol (PEG) precipitation of the serum was performed to remove immune complexes, and the supernatant of the serum run in our ELISA against the purified 0.4M-peakII. PEG 8000 (5.4%) in 0.1M sodium borate buffer was added to APSGN sera (1:10) in equal volumes and incubated at 4° C. for one hour. The sera were then centrifuged at 12,000g for ten minutes. The supernatant was assayed by ELISA using the 0.4M-peakII material as antigen (10 micrograms/ml). The final concentration of APSGN serum was 1:20. No effect on serum reactivity as judged by serum titer in the ELISA, was noted after removal of the immune complexes by this method. Finally, the possibility that the serum reactivity seen might be directed against anionic DNA contaminating the 0.4M-peakII antigen was investigated. The presence of anti-single and double stranded DNA antibodies was tested by radioimmunoassay in the laboratory of Dr. Henry Kunkel. No anti-DNA antibodies were detected in any of the acute and chronic patient sera which were highly reactive to the glomerular proteoglycan antigens.

EXAMPLE XII

Immunoblotting of the 0.6M eluate from DEAE-Cellulose chromatography of the 8M urea extracted GBM (0.6M-DE-urea-GBM) using the sera of patients with GN showed staining of a high molecular weight broad band which migrated poorly into the polyacrylamide gel. All eluates obtained from a DEAE-Cellulose column were examined by immunoblotting using a patient serum with chronic proliferative GN. This serum stained broad banded material primarily in 0.4M–0.6M eluates with little staining of the unabsorbed or 0.1M–0.2M eluates. Control studies without human sera demonstrated that this staining was not due to nonspecific binding of the alkaline phosphatase conjugated goat antihuman IgG antisera. Representative data from ELISA using 0.6M-DE-urea-GBM antigen is shown in Table XII. Fourteen of 28 chronic GN patients, but only one of 8 controls, had serum antibody titers greater than 1:50 to the 0.6M-DE-urea-GBM antigen. Some of these patients had particularly high titers of antibody in our assay, while the one control who did react had a relatively low titer of antibody (1:70). Three patients with rapidly progressive GN were studied, all of whom were known to be positive for Goodpasture's antibody by radioimmunoassay. One of these patients also had antibodies to the GBM derived proteoglycan. Rabbit antisera to human and bovine GBM reacted in very high titers (greater than 1:1000) to the 0.6M-DE-urea-GBM, while preimmune rabbit sera showed no reactivity. This data showed the cross-reactivity of the bovine and human antigens. In summary, these data demonstrated that patients with GN have antibodies to bovine GBM derived proteoglycan which are cross-reactive with human proteoglycan.

In this study, we have examined the humoral reactivity to anionic glomerular proteoglycan antigens derived from both bovine and human glomeruli. These proteoglycan antigens were isolated by 4M guanidine extraction of whole glomeruli, and further purification on DEAE-Sepharose CL-6B followed by Sepharose CL-4B chromatography. The material isolated was shown to have features characteristic of proteoglycans. High contents of glucosamine, glucuronic acid, and some galactosamine were found, in addition to protein. The purified material had a high molecular weight as noted by SDS-PAGE: molecular weight heterogeneity was noted. Staining of these gels with Alcian blue confirmed that the high molecular weight material was the isolated anionic fraction. Isoelectric focusing confirmed the anionic nature of the purified material, yielding a pI of approximately 2.9 to 3.5. Enzymatic and chemical susceptibilities confirmed the presence of heparan sulfate and either chondroitin sulfate or dermatan sulfate proteoglycans. Purified peak I material contained only glucosamine and no galactosamine, indicating the likelihood that peak I represents purified heparan sulfate proteoglycan. Whether peak II, which contains both glucosamine and galactosamine, represents a hybrid proteoglycan molecule, or two proteoglycans which cannot be separated by our methods, will require further investigations.

Immunoblotting studies with the sera of patients with various forms of GN showed reactivity to the purified broad banded heterogenous high molecular weight material isolated after Sepharose CL-4B chromatography. Using ELISA, about 50% of patients with APSGN had high titered antibodies in their serum which reacted with the glomerular proteoglycan antigen. Patients with various histologic forms of chronic GN, including patients with CPSGN, also had antibodies to this antigen, although in lower titers. Studies using both human and bovine antigenic preparations yielded similar results. In addition, rabbit antisera made to both bovine and human GBM reacted with the bovine glomerular proteoglycan to a similar degree. These studies indicate significant cross-reactivity between the human and bovine glomerular proteoglycan, and that the bovine material is useful for the detection of anti-glomerular proteoglycan antibodies in human sera in patients with various forms of GN.

The antigenic specificity of the immune reaction was further investigated by ELISA inhibition experiments which revealed the presence of two immunodeterminants. One antigenic site identified by inhibition experiments was heparan sulfate. The finding of immunoreactivity to 0.4M-peakI material, which contained no N-acetylgalactosamine, demonstrated the presence of specific immunoreactivity to heparan sulfate proteoglycan. Inhibition of immunoreactivity to the glomerular proteoglycan was demonstrated with heparan sulfate. Hyaluronate also inhibited the immunoreactivity, but was a less efficient inhibitor. Hyaluronate has a similar repeating disaccharide structure to heparan sulfate but is nonsulfated, suggesting that sulfation per se may play a role in the antigenicity of these GAGs.

These inhibition experiments also suggest cross-reactivity between heparan sulfate and hyaluronate. Since both GAG's contain a repeating disaccharide unit of N-acetylglucosamine and glucuronic acid, and both contain 1,4 linkages, either site may contribute to the cross-reactive antigen. Inhibition of immunoreactivity in patients with APSGN to heparan sulfate proteoglycan was noted with both mammalian and streptococcal hyaluronate. The streptococcus contains a capsule of hyaluronate which is identical to mammalian hyaluronate. It is conceivable that these cross-reactions between heparan sulfate and both mammalian and streptococcal hyaluronate could account for previously observed cross-reactions between streptococcal antigens and glomerular basement membrane antigens (Markowitz, A. S., et al. (1964) *J. Immunol.* 92:565-567). The monosaccharide N-acetylglucosamine did not inhibit the immunologic reaction to anysignificant degree, even at 1M concentrations. This could be explained by the observations of Kabat (Kabat, E. A., et al. (1971) Inhibition Reactions in Experimental Immunochemistry C. C. Thomas, Springfield, Ill. pp. 241-167) that the optimum binding site of polysaccharide antigens often requires multiple repeating determinants, with a certain optimum size of 4-6 molecules for the best fit into the antibody combining site. In summary, these observations indicate that antibodies to heparan sulfate of glomerular proteoglycan are found in patients with various forms of GN. Additional immunoreactivity to the protein core cannot be ruled out at this time.

The second antigenic site appears to be an immunodeterminant which is related to N-acetylgalactosamine. This was shown by inhibition experiments employing N-acetylgalactosamine and group C carbohydrate. Greater amounts of these materials were required to demonstrate inhibition on a weight basis than the heparan sulfate site, suggesting that the N-acetylgalactosamine determinant is a minor one. Galactosamine containing proteoglycan always co-migrated with the heparan sulfate proteoglycan, and represented approximately 15% of the total hexosamine in the purified material. Inhibitions with various GAG's containing N-acetylgalactosamine were essentially unremarkable, although in one experiment dermatan sulfate demonstrated some inhibition in higher concentrations. It is possible that the N-acetylgalactosamine site represents immunoreactivity to either chondroitin sulfate or dermatan sulfate which we have not been able to detect by inhibition, or possibly a galactosamine containing oligosccharide side chain of the protein core Other investigators (Couchman, J. R., et al. (1984) *Nature* 307:650-652) have shown that chondroitin sulfate is immunoreactive using monoclorial reagents, and that chondroitin sulfate is found in the glomerulus, primarily in the mesangial regions. This mesangial chondroitin sulfate proteoglycan would be present in our 4M guanidine extract of whole glomeruli. Thus, we postulate either the presence of two separate proteoglycans in our peak II preparation, or the presence of a hybrid molecule containing two different GAG chains.

The role of charge in the antibody binding to proteoglycan was investigated. ELISA studies of the specificity of this reaction revealed that the interaction was clearly not due to nonspecific charge interactions, since 1M NaCl had no effect on antibody binding. Furthermore, neither cationic immune complexes nor anti-DNA antibodies to anionic DNA were found to account for the observed reactivity. The finding of similar immunoreactivity to the 0.4M, 0.5M, and 0.6M NaCl molar eluates of the DEAE-Sepharose CL-6B chromatography further purified by Sepharose CL-4B indicates that the heterogeneous nature of the proteoglycan with respect to minor charge differences had no gross detectable influence on the overall antigenicity of the molecule. These results indicated that charge alone did not account for the observed antibody binding.

In order to further demonstrate that the glomerular proteoglycans were isolated from whole glomeruli were at least in part derived from the GBM, which is often a primary site of pathology in glomerular disease, conventional detergent procedures for the isolation of GBM were employed, followed by urea extraction, and further fractionation on DEAE-Cellulose chromatography. We noted by immunoblotting that antigenic material was being lost using this extraction method. Results in Table II demonstrate that most of the aminosugar containing material, including sulfated GAG representing primarily proteoglycans, are present in the DNase-1M NaCl and the sodium deoxcholate extract, while little (15%) material is left in the purified basement membrane which is extractable with 4M guanidine. This data further demonstrated the value of using 4M guanidine extraction of whole glomeruli for the isolation of glomerular proteoglycans in significantly larger yields. When the purified anionic fraction of the 8M urea GBM extract was used for testing in the ELISA, patients with CPSGN, proliferative GN, as well as other types of GN, were found to have antibodies in their serum to this material. However, only one of three patients with RPGN, who were known to have antibodies to Goodpasture's antigen, had antibodies to the anionic fraction of the 8M urea extract. Since Goodpasture's antigen appears to be a cationic protein (Weislander, J., et al. (1984) Supra), these data indicate that the 8M urea extract of GBM contains multiple components, and that further purification of this material yields a purified anionic fraction of GBM which is antigenically distinct from Goodpasture's antigen, and is the focus of an immune response in some patients with various types of GN, including RPGN. Finally, since similar results were obtained with proteoglycans derived from whole glomeruli and from the isolated GBM, we conclude that immunoreactivity to proteoglycan derived from whole glomeruli represents, at least in part, antibodies to GBM associated proteoglycan, as well as proteoglycans derived from other regions of the glomerulus. Proteoglycans derived from whole glomeruli appears to yield a better quantity of antigenic proteoglycan material.

The mechanism which accounts for the development of glomerular proteoglycan autoimmunity is not known. It is possible that after inflammatory injury, the exposure of hidden proteoglycan antigens to the immune system, particularly in conjunction with the onset of cross-reactive immunity incited by a streptococcal infection, could result in the onset of active autoimmunity in a genetically appropriate host. In patients with APSGN, the onset of immunity to this tissue antigen could be a harbinger of chronicity. Indeed, the finding of moderate titers of antibody to glomerular proteoglycan antigen in patients with CPSGN suggests this hypothesis could have some validity. A similar mechanism ma be operative in patients with other forms of chronic GN, and could play a role in the progression of chronic GN in these patients as well. In addition to the immunologic implications of our findings, since the glomerular heparan sulfate proteoglycan has important physiologic significance with regard to the filtration barrier function of the basement membrane (Cotran, R. S., et al. (1983) *New Engl. J. Med.* 309:1050-1052), antibodies to this antigen should also have pathophysiologic importance, particularly in regard to proteinuria.

Mammalian antigens in general may well serve as a source of antigen for GN testing.

TABLE I

ANALYSIS OF HEXOSAMINES FROM DEAE-SEPHAROSE CL-6B CHROMATOGRAPHY

| | Micromoles hexosamine | % GLCN | Micromoles hexosamine | % GALN |
|---|---|---|---|---|
| Fall Though greater than | 20 | 80 | 0.7 | 20% |
| 0.1 M NaCl elution | 0.3 | 100 | — | — |
| 0.2 M NaCl elution | 0.7 | 60 | 0.2 | 40 |
| 0.3 M NaCl elution | 0.3 | 60 | 0.1 | 40 |
| 0.4 M NaCl elution | 2.0 | 73 | 1. | 27 |
| 0.5 M NaCl elution | 5.7 | 83 | 1. | 17 |
| 0.6 M NaCl elution | 2. | 65 | 1. | 35 |
| 0.7* | 0.1 | | | |
| 0.8* | 0.1 | | | |

*For the 0.7 and 0.8 M eluates 100% of the aminosugar is glucosamine.
Aminosugars, glycosaminoglycans are seen primarily in the 0.4–0.6 M eluates in FIG. 1
GLCN = glucosamine
GALN = galactosamine

TABLE II

Chemical Composition and Properties of Bovine Glomerular Proteoglycans

| | Chemical Composition | | | |
|---|---|---|---|---|
| Sample | Protein (ug/ml) | Uronic Acid (nmoles/ml) | Glucosamine (nmoles/ml) | Galactosamine (nmoles/ml) |
| 0.4 M - peakI | 1020 | 630 | 480 | nil |
| 0.4 M - peakII | 40 | 3300 | 930 | 210 |
| 0.5 M - peakI | 200 | 480 | 455 | nil |

TABLE II-continued

Chemical Composition and Properties of Bovine Glomerular Proteoglycans

| 0.5 M - peakII | 410 | 4300 | 1300 | 300 |

Properties by susceptibility to specific enzymes and chemical treatments

| Fraction | Papain | Chondroitinase ABC | Nitrous Acid |
|---|---|---|---|
| 0.4 M - peakI | + | − | + |
| 0.4 M - peakII | + | + | + |

Similar results were obtained with 0.5 M and 0.6 M eluates of the Sepharose CL-4B column.

TABLE III

Hexosamine Content of Sequential Extractions of Human Glomeruli

| | Total Hexosamine | | Hexosamine in sulfated glycosaminoglycan | |
|---|---|---|---|---|
| Extraction | GlcN | GalN | GlcN | GalN |
| I. Whole Human Glomeruli | 10.66* | 1.45 | 5.76 | 1.39 |
| II. Sequential Extracts During Isolation of GBM: | | | | |
| A. DNase-1 M NaCl extract | 0.60 | 0.07 | 0.24 | 0.06 |
| B. Sodium Deoxycholate extract | 8.46 | 1.11 | 4.01 | 1.00 |
| III. 4 M guanidine extract of isolated GBM | 1.46 | 0.18 | 0.64 | 0.16 |
| IV. Residue | 0.14 | 0.04 | 0.04 | trace |

*all values are expressed as micromoles per gram of dry weight.
**Papain digests were fractionated on DEAE-cellulose (DE-52) and glycosaminoglycans were eluted with 2 M HCl

TABLE IVa

ELISA STUDIES OF 0.4 M - PEAKII ANTIGEN

| 0.4 M - PeakII Antigen Microgram/ml | A405 | |
|---|---|---|
| | Control Sera | APSGN Sera |
| 10 | 0.4 | 2.0 |
| 1.0 | 0.3 | 1.4 |
| 0.1 | 0.3 | 0.6 |

The antigen is titrated from 10 to 0.1 microgram/ml. Sera are from controls and patients with APSGN.

TABLE IVb

ELISA STUDIES OF 0.4 M - PEAKII (10 MICROGRAM/ML) (SERA FROM PATIENTS WITH APSGN, CPSGN AND CONTROLS)

| Serum dilution | Control | APSGN (2) Patient | | CPSGN (5) Patient | | | | |
|---|---|---|---|---|---|---|---|---|
| | | 1 | 2 | 1 | 2 | 3 | 4 | 5 |
| 1:20 | 0.35 | 2.0 | 2.0 | 0.3 | 0.3 | 0.86 | 0.95 | 1.1 |
| 1:40 | 0.37 | 1.6 | 2.0 | 0.25 | 0.27 | 0.56 | 0.60 | 0.65 |
| 1:80 | 0.30 | 0.85 | 1.71 | 0.22 | 0.3 | 0.38 | 0.45 | 0.5 |
| 1:160 | 0.30 | 0.47 | 1.18 | 0.2 | 0.3 | 0.32 | 0.38 | 0.4 |
| 1:320 | 0.20 | 0.4 | 0.5 | 0.18 | 0.25 | 0.25 | 0.3 | 0.36 |

TABLE V

| Diagnostic Group | Titer* <20 | >20 |
|---|---|---|
| ELISA Studies of 0.4 M - peakII Proteoglycan | | |
| APSGN // (7)** | 2 | 5 (148.8 ± 50.3)*** |
| CPSGN (2) | 0 | 2 (38) |
| Prol. GN (3) | 1 | 2 (38) |
| MGN (2) | 2 | 0 (−) |
| MPGN (1) | 0 | 1 (96) |
| GN-HD (1) | 0 | 1 (28) |
| All GN (16) | 5 | 11 (85.3 ± 28.4) |
| NGRD (2) | 2 | 0 |
| controls (8) | 8 | 0 |
| ELISA Studies of 0.5 M - peakII Proteoglycan | | |
| APSGN (4) | 2 | 2 (189 ± 48) |
| CPSGN (11) | 5 | 6 (40.3 ± 32.3) |
| Prol. GN (3) | 3 | 0 |
| MPGN (2) | 1 | 1 (40) |
| RPGN (1) | 1 | 0 |
| GN-HD (1) | 1 | 0 |
| All GN (22) | 13 | 9 (73.1 ± 24) |
| NGRD (2) | 2 | 0 |
| controls (13) | 12 | 1 (88) |

*titers expressed as the reciprocal of the dilution giving a absolute spectrophotometric reading of 1.0 at 405 nm.
**number of subjects
***represents the mean titer ± standard error for the patients with titer greater than twenty.
// Abbreviations used in ELISA tables RPGN—rapidly progressive GN
APSGN—acute poststreptococcal GN
CPSGN—chronic poststreptococcal GN
Prol. GN—proliferative GN
MGN—membranous GN
FGS focal glomerular sclerosis
MPGN—membranoproliferative GN
NGRD—non-glomerular renal disease
GN-HD—dialysis
GN—glomerulonephritis, not biopsie

TABLE VI

ELISA STUDIES OF 0.4 M - PEAKII (10 MICROGRAM/ML).

| Serum Dilution | A405 | | |
|---|---|---|---|
| | Rabbit Pre-immune | Anti-Bovine GBM | Anti-Human GBM |
| 1:20 | 0.25, 0.3 | 1.5 | 1.3 |
| 1:40 | 0.25, 0.3 | 1.3 | 1.18 |
| 1:80 | 0.15, 0.2 | 1.1 | 0.9 |
| 1:160 | 0.15, 0.18 | 0.8 | 0.7 |
| 1:320 | 0.18, 0.2 | 0.5 | 0.6 |

ELISA STUDIES OF 0.4 M - PEAKII (10 MICROGRAM/ML). (THE SERA OF PREIMMUNE RABBITS AND RABBITS IMMUNIZED WITH HUMAN AND BOVINE GBM ARE SHOWN. THE ANTISERUM MADE TO HUMAN GBM CROSS REACTS WITH THE BOVINE ANTIGEN)

TABLE VII

ELISA INHIBITION STUDIES OF 0.4 M - PEAKII ANTIGEN (10 MICROGRAM/ML). (AN APSGN SERUM WAS INCUBATED WITH INCREASING CONCENTRATIONS OF NACl

| APSGN Serum Dilution | PBSA, 0.5% Tween | PBSA, 0.5% Tween (0.65 M NaCl) | PBSA, 0.5% Tween (1.0 M NaCl) |
|---|---|---|---|
| 1:20 | 1.5 | 1.3 | 1.3 |
| 1:40 | 1.3 | 1.0 | 0.9 |
| 1:80 | 0.8 | 0.7 | 0.6 |
| 1:160 | 0.5 | 0.5 | 0.42 |
| 1:320 | 0.3 | 0.45 | 0.40 |

TABLE VIII

ELISA INHIBITION STUDIES OF HUMAN DE-0.6 M ELUATE (10 MICROGRAM/ML). (AN APSGN SERUM (1:40) WAS PRE-INCUBATED WITH VARIOUS PURIFIED GLYCOSAMINOGLYCANS AT VARYING CONCENTRATIONS.)

| | A405 Micrograms/ml | | | | |
|---|---|---|---|---|---|
| | 250 | 125 | 62 | 31 | 16 |
| Chondroitin-4-Sulfate | 1.87 | 1.8 | 1.82 | 1.7 | 1.8 |
| Chondroitin-6-Sulfate | 1.7 | 1.65 | 1.65 | 1.6 | 1.8 |
| Dermatan Sulfate | 1.5 | 1.5 | 1.55 | 1.6 | 1.8 |
| Heparin | 1.5 | 1.5 | 1.6 | 1.4 | 1.5 |
| Bovine Hyaluronate | 1.3 | 1.4 | 1.5 | 1.6 | 1.8 |
| Heparan Sulfate | 0.8 | 0.9 | 1.0 | 1.0 | 1.4 |
| Control (APSGN 1:40 Alone) | 1.7 | 1.7 | 1.7 | 1.7 | 1.7 |

TABLE IX

ELISA INHIBITION STUDIES OF HUMAN DE-0.6 M ELUATE (10 MICROGRAM/ML) (AN APSGN SERUM 1:40 WAS PRE-INCUBATED WITH HEPARAN SULFATE GLYCOSAMINO-GLYCAN (HeS) BOVINE HYALURONATE [HYA (BOV)] AND STREPTOCOCCAL HYALURONATE [HYA (STR)] AT VARYING CONCENTRATIONS.

| | A405 mg/ml | | | | | | | | | |
|---|---|---|---|---|---|---|---|---|---|---|
| | 10 | 5 | 2.5 | 1.5 | 0.62 | 0.325 | 0.162 | 0.082 | 0.041 | 0.022 |
| APSGN Sera (1:40) | 1.6 | 1.6 | 1.6 | 1.6 | 1.6 | 1.6 | 1.6 | 1.6 | 1.6 | 1.6 |
| +HeS | | | | | 0.75 | 0.8 | | 0.85 | 1.1 | 1.5 |
| +Hya (Bov) | | 0.8 | 0.85 | 0.9 | 1.1 | 1.2 | | | | |
| +Hya (Str) | 0.5 | 0.5 | 0.55 | 0.6 | 0.75 | | | | | |

TABLE X

ELISA INHIBITION STUDIES OF 0.4 M - PEAKII ANTIGEN (10 MICROGRAM PER ML) [AN APSGN SERUM (1:40) WAS PREINCUBATED WITH VARIOUS INHIBITORS: DERMATAN SULFATE (DeS), N-ACETYL GLUCOSAMINE (N-GLU N), N-ACETYL GALACTOS-AMINE (N-GAL N), STREPTOCOCCAL HYALURON-ATE (STR. HYA.) AND HEPARAN SULFATE (HeS)]

| | A405 APSGN Serum Dilution | | |
|---|---|---|---|
| | 1:40 | 1.80 | 1:160 |
| Serum | 1.8 | 1.3 | 0.8 |
| Serum + DeS (0.25 mg/ml) | 1.5 | 1.1 | 0.75 |
| Serum + N-glu N (1 M) | 1.25 | 0.9 | 0.6 |
| Serum + N-gal N (1 M) | 1.05 | 0.75 | 0.4 |
| Serum + Str. Hya. (5 mg/ml) | 0.8 | 0.5 | 0.4 |
| Serum + HeS (0.25 mg/ml) | 0.4 | 0.38 | 0.35 |
| Serum + N-gal N (1.0 M) and Str. Hya. (5 mg/ml) | 0.3 | 0.3 | 0.3 |

TABLE XI

| Inhibition of ELISA Reactivity to Human DE-0.6 M Antigen | |
|---|---|
| Inhibitor | Percent Inhibition |
| Heparan sulfate GAG (0.1 mg/ml) | 51.3% |
| Streptococcal Hyaluronate (5 mg/ml) | 68% |
| Human umbilical cord hyaluronate (5 mg/ml) | 48% |
| Group C streptococcal carbohydrate (5 mg/ml) | 56% |
| Group A streptococcal carbohydrate (5 mg/ml) | 9% |
| Group A variant strep. carbohydrate (5 mg/ml) | 9% |

The serum from a patient with APSGN at a 1:40 dilution was used for these studies.

TABLE XII

ELISA Studies of Bovine 0.6 M-DE-urea GBM Antigen*

| | Serum Titer | | |
|---|---|---|---|
| Diagnostic Group | <50 | 50–100 | >100 |
| RPGN (3) | 2 | 0 | 1 |
| Prol. GN (3) | 0 | 1 | 2 |
| APSGN (2) | 0 | 0 | 2 |
| MGN (4) | 3 | 1 | 0 |
| FGS (2) | 1 | 1 | 0 |
| MPGN (2) | 1 | 1 | 0 |
| GN-HD (6) | 3 | 1 | 2 |
| GN (6) | 4 | 0 | 2 |
| All GN (28) | 14 | 5 | 9 |
| controls (8) | 7 | 1 | 0 |

*Results are expressed as in Table IV.
Abbreviations as shown on Table V.

What is claimed is:

1. A kit for the diagnosis of acute or chronic human post-streptococcal glomerulonephritis which comprises purified bovine or human anionic, solubilizable glomerular glucosamine or galactosamine containing proteoglycan antigens of about 200,000 molecular weight wherein the ratio of glucosamine:galactosamine is approximately 4.5:1 and said antigen is capable of immunologically reacting with human IgG and IgM antibodies in human sera in patients with post-streptococcal glomerulonephritis.

* * * * *

UNITED STATES PATENT AND TRADEMARK OFFICE
CERTIFICATE OF CORRECTION

PATENT NO. : 4,985,542
DATED : January 15, 1991
INVENTOR(S) : Howard Fillit, et al.

It is certified that error appears in the above-identified patent and that said Letters Patent is hereby corrected as shown below:

| | |
|---|---|
| Abstract, line 4: | change "area" to -- sera --. |
| Col. 1, line 12: | after "4,849,339" insert -- issued July 18, 1989 --. |
| Col. 3, line 23: | change "ure" to -- urea --. |
| Col. 4, line 29: | change "electrohporesis" to -- electrophoresis --. |
| Col. 4, line 53: | after "0.1M" delete "H" and insert -- $H_2SO_4$ --. |
| Col. 9, line 59: | change "III" to -- VIII --. |
| Col. 10, line 28: | change "XI" to -- X --. |
| Col. 12, line 52: | change "167" to -- 267 --. |
| Col. 13, line 15: | change "monoclorial" to -- monoclonal --. |
| Col. 16, Table V, line 39: | change "biopsie" to -- biopsied --. |

UNITED STATES PATENT AND TRADEMARK OFFICE
CERTIFICATE OF CORRECTION

PATENT NO. : 4,985,542
DATED : January 15, 1991
INVENTOR(S) : Howard Fillit, et al.

It is certified that error appears in the above-identified patent and that said Letters Patent is hereby corrected as shown below:

Col. 18, line 63,
   Claim 1:        change "antigens of about" to -- antigens greater than --.

Signed and Sealed this

Ninth Day of February, 1993

Attest:

STEPHEN G. KUNIN

Attesting Officer     Acting Commissioner of Patents and Trademarks